(12) United States Patent
Li et al.

(10) Patent No.: US 8,771,980 B2
(45) Date of Patent: Jul. 8, 2014

(54) COMBINED LIQUID TO SOLID-PHASE ANAEROBIC DIGESTION FOR BIOGAS PRODUCTION FROM MUNICIPAL AND AGRICULTURAL WASTES

(75) Inventors: Yebo Li, Wooster, OH (US); Jiying Zhu, Wooster, OH (US); Caixia Wan, Wooster, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 19 days.

(21) Appl. No.: 13/396,293

(22) Filed: Feb. 14, 2012

(65) Prior Publication Data

US 2012/0231494 A1 Sep. 13, 2012

Related U.S. Application Data (63) Continuation of application No. PCT/US2010/045447, filed on Aug. 13, 2010.

(60) Provisional application No. 61/234,165, filed on Aug. 14, 2009.

(51) Int. Cl.
| | | |
|---|---|---|
| C02F 3/28 | (2006.01) |
| C10L 5/44 | (2006.01) |
| C12P 5/02 | (2006.01) |
| C05F 17/00 | (2006.01) |
| C10L 5/36 | (2006.01) |
| C10L 3/08 | (2006.01) |

(52) U.S. Cl.
CPC . *C12P 5/023* (2013.01); *C10L 5/44* (2013.01); *Y02E 50/30* (2013.01); *C05F 17/0027* (2013.01); *Y02E 50/343* (2013.01); *C05F 17/0018* (2013.01); *C10L 5/363* (2013.01); *C10L 3/08* (2013.01); *Y02E 50/10* (2013.01); *C02F 3/28* (2013.01)

USPC ........ 435/51; 435/183; 435/289.1; 435/286.1

(58) Field of Classification Search
CPC ...................................... C12P 5/02; C02F 3/28
USPC ............................................................ 435/41
See application file for complete search history.

(56) References Cited

U.S. PATENT DOCUMENTS

| | | |
|---|---|---|
| 4,684,468 A | 8/1987 | DeBaere |
| 5,500,306 A | 3/1996 | Hsu et al. |
| 6,342,378 B1 * | 1/2002 | Zhang et al. .................. 435/168 |
| 6,454,944 B1 | 9/2002 | Raven |
| 6,521,129 B1 | 2/2003 | Stamper |
| 6,569,332 B2 * | 5/2003 | Ainsworth et al. ........... 210/603 |
| 6,730,223 B1 | 5/2004 | Anderson |
| 7,708,885 B2 | 5/2010 | Lanting |

OTHER PUBLICATIONS

De Gioannis et al., Two-phase anaerobic digestion within a solid waste/wastewater integrated management system, Waste Management, Jan. 2008, vol. 28, p. 1801-1808.*

* cited by examiner

*Primary Examiner* — Taeyoon Kim
*Assistant Examiner* — Tiffany Gough
(74) *Attorney, Agent, or Firm* — Standley Law Group LLP (57) ABSTRACT

Biogas is obtained in a solid-state anaerobic digester from a solid organic biomass and a digestion effluent produced in an associated liquid anaerobic digester. The solid organic biomass and digestion effluent are mixed to produce an effluent-biomass mixture. The effluent-biomass mixture is then incubated in the solid state anaerobic digester, producing a biogas and a digestate. The incubation is controlled by adjusting the composition and properties of the effluent-biomass mixture. The solid organic biomass may comprise lignocellulosic biomass, food waste, agricultural waste and the like.

17 Claims, 7 Drawing Sheets

COMBINED LIQUID TO SOLID-PHASE ANAEROBIC DIGESTION FOR BIOGAS PRODUCTION FROM MUNICIPAL AND AGRICULTURAL WASTES

CROSS-REFERENCE TO RELATED APPLICATIONS

This application is a continuation of, and claims the benefit of priority to, PCT/US2010/045447, filed on 13 Aug. 2010, which in turn claims the benefit of priority to U.S. Ser. No. 61/234,165, filed on 14 Aug. 2009. Both applications are incorporated by reference as if fully recited.

TECHNICAL FIELD

Embodiments are in the field of waste removal and energy production, more particularly in the field of anaerobic digestion for energy production.

BACKGROUND OF THE ART

Renewable energy and products are playing an increasingly important role in today's world. Valuable products, such as methane, can be produced from renewable organic materials, such as biomass, by biological conversion processes.

Anaerobic digestion has been recognized to be able to stabilize sludge and other predominantly organic materials, and produce usable product gas of varying composition. Anaerobic digestion uses a consortium of natural bacteria to convert organic waste to carbon dioxide and methane in the absence of oxygen, which is accomplished by a consortium of microorganisms working synergistically, involves four steps, namely hydrolysis, acidogenesis, acetogenesis, and methanogenesis, of which hydrolysis is the most rate-limiting stage.

Anaerobic digestion systems can be separated into two major types, one phase systems and two phase systems. In one phase systems, acidogenesis and methanogenesis microorganisms are housed in the same vessel. In the two phase systems, acid-forming phase is separated from a methane-forming phase, so that each phase can be operated more efficiently. In the first phase, organic substrate is liquefied and broken-down into lower molecular weight and other intermediates which are converted to methane in the second phase.

In conventional liquid anaerobic digestion (AD) facilities, the digesters are operated with a total solid content of 0.5% to 15%. Typical liquid AD produces a large amount of effluent which normally contains a high amounts of ammonium, phosphate, suspended solids and dissolved solids, has been applied as fertilizer. However, there is a limit to the distance that this effluent can be transported and applied economically, and there is often not enough farmland in the adjoining territory to make use of the total effluent. Additionally, excessive application of post-digestion effluent on agricultural land has resulted in nutrient overloading and sediment pollution in local watersheds.

Thus, the effluent of liquid AD is often treated prior to discharge creating an economic barrier to the use of this technology both as a waste management tool and as an energy production tool. Solid-liquid separation followed by membrane separation of the effluent produces an organic fertilizer and clear water, however, this process is costly and flocculants are generally employed to increase the efficiency of the separation. These flocculants create their own problems as un-reacted acrylamide monomers remaining in the added polymers have been shown to be carcinogenic, although the polymers themselves are harmless. In addition, the polymers are non-biodegradable posing another hurdle for the use of the effluent as a fertilizer. In all, the handling of the effluent of liquid AD is a major hurdle for the use of liquid AD.

In contrast to liquid AD systems, solid state anaerobic digestion (SS-AD) systems operate with 15-40% total solids, making them suitable for processing the organic fraction of municipal solid waste (MSW). SS-AD systems have several advantages over liquid AD systems including: smaller volume; less energy consumption for heating; no processing energy for stirring; and reduced material transportation costs. Due to the lower water content, the digestate of SS-AD process can be used as fertilizer or pelletized for use as a fuel, making the residue of the process much easier to handle than that of the liquid AD processes.

Disadvantages of conventional SS-AD systems include the large amount of inoculum required for efficient digestion, longer retention time (three times that of liquid AD), and the requirement of nitrogen nutrients supplementation when lignocellulosic biomass is used.

If operational conditions (pH, C:N ratio, solid content, and temperature) are not maintained at optimal values, imbalances among microorganisms can lead to digester upset (failure) as a result of buildup of organic acids which can inhibit the methanogen activity.

SUMMARY

This and other unmet needs of the prior art are met by the system and method as described in more detail below.

Embodiments relate to a process and a system for the production of biogas from solid organic material. In particular, embodiments may be used to generate biogas from lignocellulosic biomass. The disclosed embodiments describe a novel process and system which exploit the synergistic combination of a liquid AD system and a SS-AD system. The novel processes and systems effectively recycle the liquid digestion effluent from a liquid AD and use it as inoculum for a SS-AD, thereby several barriers in the use of SS-AD are overcome at once. Additionally, the use of effluent as inoculum eliminates the need for nitrogen supplementation in the SS-AD process. The two processes may run in parallel each contributing to a combined heat and power (CHP) unit for the production of electricity. In addition, the heat from the combined heat and power (CHP) unit may be used to promote the digestion processes in the SS-AD and or the liquid AD.

Disclosed embodiments employ a solid state anaerobic digester which converts a mixture of digestion effluent from a liquid AD and a solid organic material (e.g., a ligno-cellulosic biomass, food waste, agricultural waste, etc.) to a biogas. Embodiments use the effluent of liquid AD as a nitrogen source and inoculum for solid state digestion. Instead of using digested solids or recycling SS-AD leachate to inoculate the raw materials as in conventional systems, effluent of liquid AD is used to inoculate the solid organic material. The liquid state anaerobic digester can be either one-phase or two-phase system which uses any feedstock suitable for liquid AD such as sewage sludge, animal manure, food waste or another organic waste. The effluent after liquid AD digestion generally has high nitrogen content.

Accordingly, embodiments relate to an innovative SS-AD system that overcomes the major barriers for liquid AD (i.e., treatment of effluent) and current SS-AD systems (i.e., requirement of inoculum and nitrogen supplementation). Embodiments may substantially reduce production cost and increase the energy efficiency of methane production.

BRIEF DESCRIPTION OF THE DRAWINGS

A better understanding of the inventive concept will be obtained when reference is made to the appended drawings, where identical parts are identified by identical reference numbers and where.

DESCRIPTION

Embodiments provide improved methods for the anaerobic digestion of waste to produce biogas along with compositions and systems with which to perform these methods.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The section headings used herein are for organizational purposes only and are not to be construed as limiting the described subject matter in any way. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

As used herein, a liquid state anaerobic digester ("AD") is a digester that operates using a liquid feedstock. The liquid feedstock has a total solid concentration of about 0.5% to less than about 15%. Liquid state anaerobic digestion is commonly referred to in the art as "wet" digestion.

As used herein, a solid-state anaerobic digester ("SS-AD") is a digester for digesting solid organic materials. Typical feedstocks have a total solids concentration greater than about 15% to about 50%, preferably between about 20% to about 40%. Feedstocks with solids concentrations above 50% are also possible.

Embodiments can be practiced with any carbonaceous organic substrate including, but not limited to, sewage sludge, forestry waste, food waste, agricultural waste, municipal waste, and the like.

Municipal waste primarily contains cellulosic products food wastes, grass clippings, tree trimmings, and paper products. It is known that such cellulosics can be digested as well as the minor amounts of waste protein, carbohydrates and fat present in municipal waste.

In various embodiments, the organic substrate comprises, at least in part, an agricultural waste. Agricultural wastes include both plant and animal wastes. Many types of agricultural waste can be used in conjunction with the embodiments. Useful agricultural wastes include, but are not limited to, foliage, straw, stalks, husks, fruit, manure and the like.

Embodiments use the digestion effluent from an operational liquid AD system as a source of inoculum for a SS-AD process. In order to be effective as inoculum, the effluent should contain viable microorganisms. The liquid AD digestion effluent can be expected to contain acid forming bacteria and methane-producing organisms. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385-416, Pergamon Press (1969). As set forth in that review, the principal suitable acid forming species include, species from genera including, but not limited to, *Aerobacter, Aeromonas, Alcaligenes, Bacillus, Bacteroides, Clostridium, Escherichia, Klebsiella, Leptospira, Micrococcus, Neisseria, Paracolobacterium, Proteus, Pseudomonas, Rhodopseudomonas, Sarcina, Serratia, Streptococcus* and *Streptomyces*. Also of use in the embodiments are microorganisms which are selected from the group consisting of *Methanobacterium oinelianskii, Mb. formicium, Mb. sohngenii, Methanosarcina barkeri, Ms. methanica* and *Mc. mazei* and mixtures thereof. Other useful microorganisms and mixtures of microorganisms will be apparent to those of skill in the art.

An operative mixed culture is capable of sustaining itself indefinitely as long as a fresh supply of organic materials is added because the major products of the fermentation are gases, which escape from the medium leaving little, if any, toxic growth inhibiting products. Mixed cultures generally provide the most complete fermentation action. Nutritional balance and pretreatment can be made as is known in the art to favor hydrolytic activity.

The microbiome of SS-AD is expected to differ somewhat from that driving a liquid AD system because of the differences in physical and chemical parameters between SS-AD and liquid AD, particularly low water activity, limited mass transfer, and restricted accessibility of microbes to the solid substrates in dry digesters. Even so, embodiments demonstrate that the liquid AD digestion effluent contains the pertinent guilds of microbes for SS-AD. Although supplemental inoculation, beyond the effluent inoculums itself, is not required, the addition of desirable microorganisms may be useful for improving the efficiency of the process in certain applications.

Embodiments operate at a constant or variable temperature between about 10° C. to about 70° C., more preferably between about 35° C. to about 65° C., and most preferably between about 37° C. to about 60° C. Various embodiments operate at mesophilic or thermophilic temperatures.

The term biogas as used herein refers to gas comprising methane. A sustainable way of obtaining biogas is by the anaerobic digestion of a biomass. Lignocellulose is a complex fibrous structure of the sugar polymers cellulose and hemicellulose, strongly intermeshed with the aromatic copolymer lignin. Both lignin and holocellulose are very abundant biopolymers and are present in most forms of biomass.

Mechanical or chemical treatment of the organic substrate may be required either to achieve a particle size and or microstructure appropriate for use in anaerobic digestion according to the embodiments or to render the carbonaceous components of the organic substrate more accessible to the digestion media. Suitable methods of mechanical and chemical treatment are known in the art. Various pretreatment of the organic substrate can advantageously be used with the embodiments, such as alkaline pretreatment.

Most conventional SS-AD reactors use food waste, organic fraction of municipal solid waste, or corn silage as feedstock, which do not need pretreatment. However, lignocellulosic biomass, such as corn stover and yard waste, is a heterogeneous polymer of cellulose and hemicelluloses and lignin. The complex structure of native lignocellulosic materials creates recalcitrance to enzymatic hydrolysis of cellulolytic microbes in the anaerobic digester. Additionally, due to the low cellulolytic activity and slow specific growth rates of cellulolytic microbes, the anaerobic fermentation efficiencies of native lignocellulosic materials are usually very low in conventional bioreactors. Pretreatment has been proven to be effective in increasing the efficiency of anaerobic digestion of lignocellulosic biomass in SS-AD. However, the pretreatment process generally has high capital and operational cost.

Lignocellulosic biomass has a high carbon to nitrogen ratio (C:N) (around 50 for corn stover). To obtain an optimal C:N ratio for anaerobic digestion of around 25, supplementation of nitrogen source such as $NH_4Cl$ is required in conventional SS-AD systems. However, after the carbon source is converted to biogas, the effluent of liquid AD generally has a low C:N ratio (typically below 10). In disclosed embodiments, the use of effluent of liquid AD overcomes the high C:N ratio obstacle. In disclosed embodiments the liquid effluent may be mixed with lignocellulosic biomass such as crop residues, yard trimming, energy crops, wood residues and waste both during an initial mixing stage and or during intermittent supplementations during digestion. Thus, when liquid AD effluent was used as inoculum for SS-AD, the C:N ratio of the mixture reached an optimal value between 20-30 and supplementation of nitrogen was not needed.

Generally, SS-AD processes, when performed in batch, are susceptible to termination due to rapid pH drop. This problem is often avoided by supplementation with further alkali beyond that in a pretreatment step. However, in an embodiment of the present system, a small fraction of liquid AD effluent may be added at least once after initiation of the SS-AD batch operation to improve the stability of the SS-AD process, thus the effluent can take the place of the alkali further reducing the capital cost associated with SS-AD. One method of implementation is to add the effluent through injection pipes on the lid. Effluent can be added intermittently (every 1-10 days, preferably 3-5 days) during the batch operation of the SS-AD process.

In disclosed embodiments, injection pipes may extend into the solid organic material to deliver liquid AD digestion effluent into the solid organic material during the SS-AD process. The portion of injection pipes which is immersed into the materials may be perforated to allow optimal distribution of the effluent into the SS-AD reactor.

In conventional SS-AD processes, part of the digestate needs to be recycled and mixed with the new feedstock at a ratio of 1:5-6 (feedstock:digestate). However, digestate recycling substantially reduces reactor utilization efficiency. Advantageously, disclosed embodiments overcome this obstacle. When the liquid AD effluent is used as inoculum there is no need to recycle the digestate of SS-AD.

Disclosed embodiments eliminate the need for mixing or leachate recycling during the SS-AD process. Conventional material mixing during the SS-AD process is complicated and costly. Additionally, a batch or single phase digester may suffer from a pH drop which can terminate the SS-AD process. Prior SS-AD systems have adopted leachate or digestate recycling to increase the stability of the SS-AD process. However, leachate recycling generates reduces the solid content of the digestate of SS-AD. Digestate recycling (often requiring 5-6 fold increases in raw material) can produce compost like digestate, but it substantially reduced the reactor utilization efficiency. However, in the disclosed embodiments, when the liquid AD effluent may be intermittently added during the SS-AD process to improve the process stability; this has an added benefit as there is no leachate in the digestate of the disclosed embodiments, which has significant economic and environmental benefits.

For example, when corn stover was mixed with liquid AD effluent at corn stover/effluent (vs/vs) ratio higher than 2.5, no leachate is observed in the SS-AD reactor. As noted above, at thermophilic temperatures, batch operations may suffer from a sudden pH drop; however, if only a small fraction of liquid AD effluent is added during the SS-AD batch operation, the SS-AD process remains stable at thermophilic temperatures and the biogas yield increased by 20-30% compared to those obtained at mesophilic temperatures. Disclosed embodiments utilize a reactor design with injection pipes on the lid to effectively mix the liquid AD effluent with the corn stover.

Digestate of the proposed SS-AD system has high solid content which can be used as fertilizer or to be pelletized as fuel. When effluent of liquid AD and corn stover is mixed at a ratio of 2.5 to 5 (vs/vs) the lignin content of the SS-AD digestate reached about 30-40%, which makes it a good feedstock to be used as fuel for burners. The digestate of the SS-AD system may be pelletized as fuel.

The feedstock/effluent mixing ratio determines the solid content, C:N ratio, and food to microorganism ratio (F/M) of SS-AD, and as a result of the performance of SS-AD. Mixture of effluent of the liquid anaerobic digestion with lignocellulosic biomass at different ratio will obtain a solid concentration ranging from 20-50% (preferably 20-30%), which is favorable for the solid state anaerobic digestion. Biogas yield of 0.35 L/kg of volatile solids (VS) was achieved when a corn stover/effluent mixing ratio of 2.5 was used. At this mixing ratio the C:N ratio and solid content were 16 and 22%, respectively. Increasing the mixing ratio will increase the solid content of the digestate which may further reduce overall shipping and processing cost.

In various embodiments, the solid state anaerobic digestion can digest waste at mesophilic temperatures (30-40° C.). Preferably, the system runs at 37-42° C. The solid state anaerobic digestion may also be run at thermophilic conditions (40-60° C.). Particularly at thermophilic conditions (40-60° C.), the supplemental addition of liquid AD digestion effluent through injection pipes on the lid of the SS-AD digester can increase the stability of the SS-AD process. In various embodiments, effluent may be added intermittently (e.g., every 1-10 days, 3-5 days, etc.) during the batch operation of the SS-AD process.

In various embodiments, mechanical size reduction of the biomass will also help with the biodegradation by rupturing the cell walls and making the biodegradable components more accessible to microorganisms. Thus, in a various embodiments, the biomass is pretreated by a physical process selected from the group consisting of shredding, grinding, cutting, and combinations thereof. In another embodiment, the biomass is pretreated using a method comprising grinding the cellulosic biomass to a size from about 2 millimeters to about 50 millimeters. Preferably, the biomass is ground and or cut to about 5-30 mm pieces. In one embodiment, the biomass may be ground and or cut to about 10-25 mm pieces.

In some embodiments, mechanical mixing may be used to mix or contact the effluent and or pretreatment chemicals (e.g., alkali) with the biomass. Mixing may be performed in the SS-AD or in an external mixing chamber. Means for mixing may include industrial batch mixers, agitators, blade mixers, etc.

When employed at thermophilic temperatures (e.g., 55° C.), disclosed embodiments of a solid state digester may have a higher chemical oxygen demand (COD) removal, pathogen removal, and biogas yield than the mesophilic digester (30-40° C.). However, a thermophilic digester requires more energy for heating and has a higher probable risk of buildup of organic acid (pH drop) which suppresses methanogen organisms. Disclosed embodiments may be conducted at both mesophilic digestion (37° C.) and thermophilic digestion (e.g., 55° C.) conditions. NaOH addition at a rate of 0.05 g/g corn stover achieved 33% increase in biogas yield compared to non-treated corn stover at the mesophilic condition (37° C.).

The biogas produced from the SS-AD process can be collected and directed to an optional combined heat and power (CHP) unit. The CHP unit may be employed to produce electricity and provide supplemental heat to drive the digestion processes. The digestate of the SS-AD process can be used as a fertilizer, animal bedding or pelletized to be used as a fuel.

Lignocellulosic biomass used in the disclosed embodiments may also include OFMSW either source separated or mechanical separated. When OFMSW is used instead of corn stover, as OFMSW contains more nitrogen than corn stover, the ratio of liquid AD effluent to OFMSW need to be calculated and tested to obtain the optimal C:N around 25 for the SS-AD.

Various embodiments include the following.

A method for producing a biogas from a solid organic biomass using a digestion effluent of a liquid anaerobic digester, comprising: providing the digestion effluent of a liquid anaerobic digester; mixing the solid organic biomass with the digestion effluent to generate an effluent-biomass mixture; and incubating the mixture in a solid state anaerobic digester to produce a biogas and a digestate.

A method according to the paragraph above, further comprising the step of: directing the biogas produced during the incubating step to a combined heat and power unit.

A method according to any of the paragraphs above, wherein: the mixing step is performed outside the solid state anaerobic digester.

A method according to any of the paragraphs above, further comprising the step of: cutting or grinding the biomass prior to the mixing step.

A method according to the paragraph above, wherein the cutting or grinding step is performed until the biomass comprises particles with an average size from about 2 millimeters to about 50 millimeters.

A method according to any of the paragraphs above, wherein: the biomass comprises a lignocellulosic material.

A method according to any of the paragraphs above, further comprising the step of: pretreating the biomass with alkali.

A method according to any of the paragraphs above, further comprising the step of: dewatering the effluent prior to the mixing step.

A method according to any of the paragraphs above, wherein the incubating step further comprises the step of: adding a supplemental portion of the digestion effluent to the mixture during the incubating step.

A method according to the paragraph above, wherein the adding step is performed intermittently during the incubating step.

An integrated anaerobic digester system for production of biogas from a solid organic biomass using a digestion effluent from a liquid anaerobic digester, said system comprising: a solid waste digestion reactor comprising an effluent inlet, a cover, and a reaction vessel, the vessel comprising therein the digestion effluent from a liquid anaerobic digester and a solid organic biomass; and a conduit in fluid communication with the effluent inlet; and the liquid anaerobic digester comprising an outlet in fluid communication with the conduit.

The system according to the paragraph above, further comprising: a pump integrated along the conduit, the pump oriented to receive digestion effluent from the liquid anaerobic digester and impel it toward the solid waste digestion vessel.

The system according to any of the paragraphs above, further comprising: a mixing chamber integrated along the conduit, the mixing chamber comprising means for mixing the solid organic biomass with the digestion effluent.

The system according to any of the paragraphs above, further comprising: a size reduction unit comprising means for chopping or grinding the solid organic material to reduce particle sizes.

The system according to any of the paragraphs above, further comprising: a pretreatment holding chamber connected to the mixing chamber comprising therein an alkali and the solid organic material.

The system according to any of the paragraphs above, further comprising: a combined heat and power unit in communication with the solid state anaerobic digester.

The system according to the paragraph above, wherein: the communication comprises at least one of biogas communication and hot water communication.

A composition for generating a biogas, comprising: a digestion effluent from a liquid anaerobic digester; and a solid organic biomass.

A composition according to the claim above, wherein: the solid organic biomass comprises cellulose, hemicellulose, and lignin.

Figure 1:
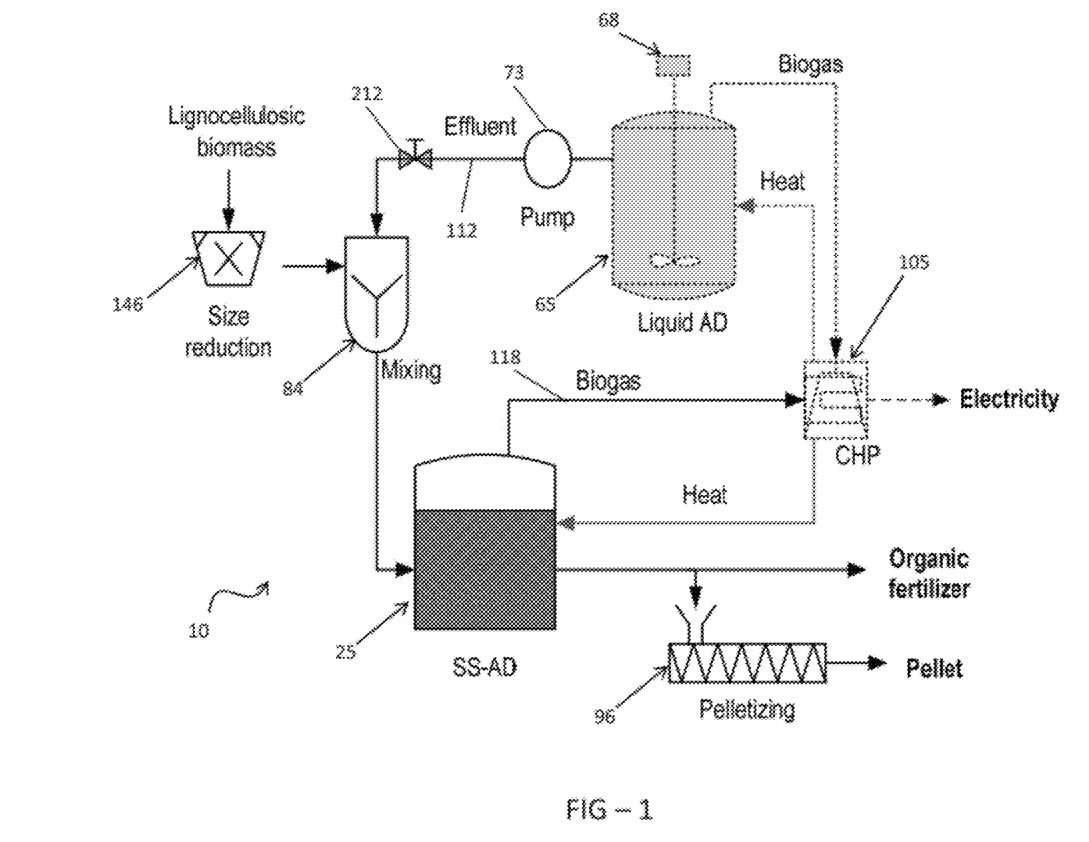
FIG. 1 is a schematic drawing of exemplary embodiment of the integrated anaerobic digester system.

With reference to the figures, FIG. 1 shows an exemplary system 10 for converting lignocellulosic material into biogas. The exemplary system comprises a solid state anaerobic digester ("SS-AD") 25 in fluid communication with a liquid state anaerobic digester ("liquid AD") 65. The liquid AD system 65 comprises a liquid AD mixer 68 capable of continuous mixing in the liquid AD 65 reaction chamber. The liquid AD 65 can be either a one-phase or two-phase system and may use any feedstock suitable for liquid AD, including, but not limited to, sewage sludge, animal manure, food waste or another organic waste. The effluent after liquid AD digestion generally has high nitrogen content. As shown in FIG. 1, a pump 73 may be located along the conduit and positioned to impel liquid AD digestion effluent from the liquid state anaerobic digester 65 through effluent line 112 into a mixing chamber 84 where the effluent and a lignocellulosic material may be mixed. Effluent line 112 may comprise an effluent valve 212 to regulate effluent flow into the mixing chamber 84. Mixture of effluent of the liquid anaerobic digestion with lignocellulosic biomass at different ratio will obtain a solid concentration ranging from about 20-50% (preferably 20-30%), which is favorable for the solid state anaerobic digestion. If the total solids of the effluent from the liquid digester is too low, an optional dewatering process may be included to remove some of the water before it is mixed with the lignocellulosic biomass.

In specific embodiments, the liquid AD and the SS-AD reactor may be connected via at least one conduit through which effluent from the liquid AD reactor can be transferred to the SS-AD reactor. The liquid AD reactor and the SS-AD reactor may be connected in any useful arrangement. In an alternative embodiment, digestion effluent from the liquid AD reactor may be transported separately to the SS-AD.

The biomass may be ground and chopped to reduce the particle size of the biomass prior to or concurrent with mixing. In the example shown in FIG. 1, the biomass can be cut and or ground with a size reduction unit 146, prior to entering the mixing chamber 84. Means for chopping or grinding the solid organic material may include, for example, blades and or a pulvarizer. In various embodiments, the cellulosic biomass is ground and or cut to about 2-50 mm pieces. Preferably, the biomass may be ground and or cut to about 10-25 mm pieces. After mixing in the mixing unit 84, the resultant effluent-biomass mixture may then be fed into the SS-AD 25.

In the SS-AD 25, the effluent-biomass mixture is converted into a biogas and a digestate. Optionally, the generated biogas may exit the SS-AD through biogas line 118 into a combined heat and power unit ("CHP") 105. The heat generated from the CHP may be used to supply heat for digestion in the liquid AD and or the SS-AD.

The digestate of the SS-AD process itself is a useful by-product which can be used, for example, as a fertilizer, animal bedding, and or pelletized into fuel, etc., in a pelletizer 96. An exemplary embodiment may be used for mesophilic and/or thermophilic SS-AD processes.

As shown in FIG. 1, the system may be constructed so that the SS-AD and liquid AD components share the same CHP 105, which may reduce the capital investment for the CHP unit. In the embodiment, effluent of liquid AD is used as inoculum and as a nitrogen source for the SS-AD process; therefore, the current costly solid/liquid separation and membrane filtration system used for treatment of liquid AD effluent is unnecessary. The digestate of SS-AD can be used as an organic fertilizer or be pelletized to be used as fuel.

Figure 2:
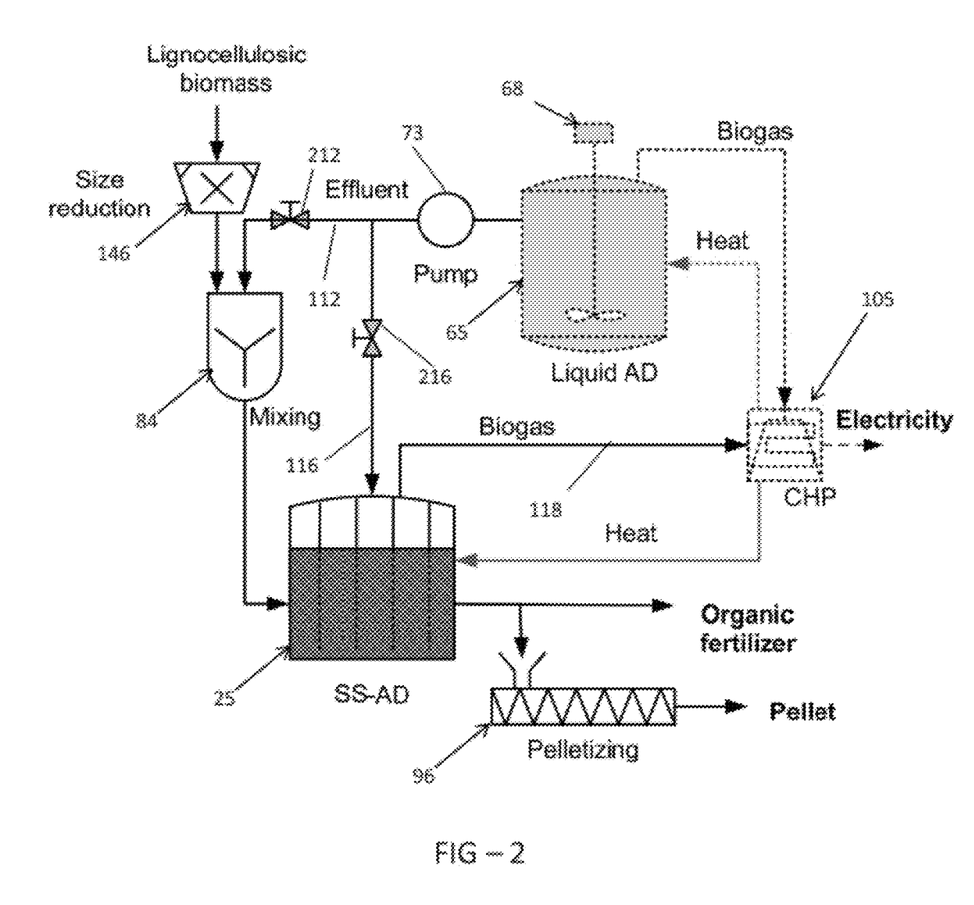
FIG. 2 is a schematic drawing of another embodiment in which supplemental effluent is added directly during SS-AD digestion.

FIG. 2 shows an embodiment for the addition of supplemental effluent. In various embodiments, supplemental effluent may be added to supplement digestion in the SS-AD reactor 25. In such embodiments, effluent may be added intermittently throughout the SS-AD incubation period. Particularly at thermophilic conditions (e.g., 55° C.), intermittent addition of supplemental effluent may prevent premature failure of the SS-AD process, often caused by a precipitous drop in the pH level within the reactor. In specific embodiments, effluent may be added intermittently every 1-10 days, preferably every 3-5 days or more often. The supplementation schedule, the supplemental effluent flow rate, and the effluent injection pressure may be optimized for each application based on characteristics of the reactor and the relevant biomass. FIG. 2 shows one embodiment for the addition of supplemental effluent, many others are possible. As illustrated, effluent may be shunted from a first conduit into a supplemental effluent line 116 that is in fluid communication with the SS-AD reactor 25. The supplemental effluent line 116 may comprise a supplemental effluent valve 216 to regulate the flow of supplemental effluent into the SS-AD reactor 25. Repeated elements from FIG. 1 are not discussed.

Figure 3:
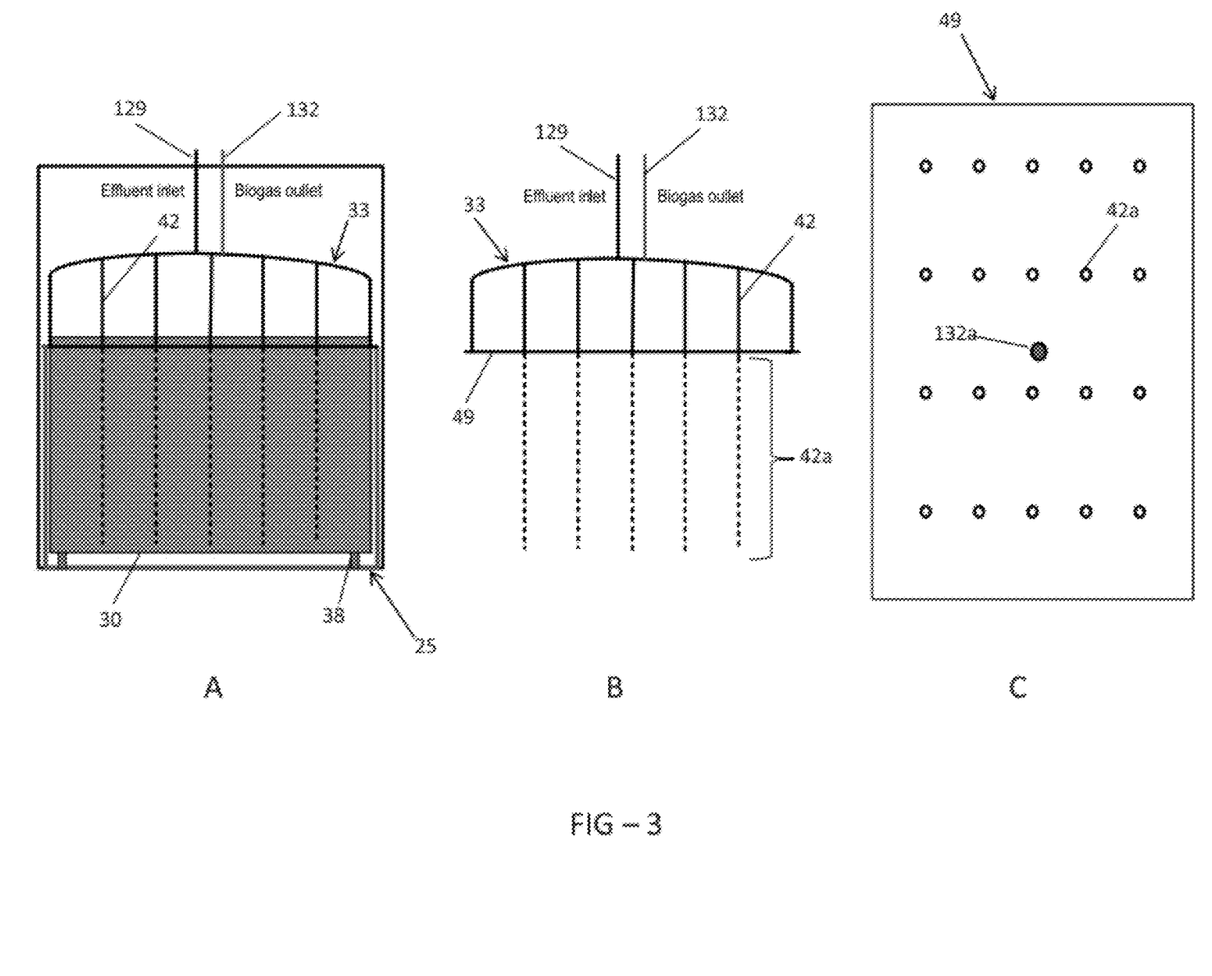
FIG. 3 is a schematic of an exemplary SS-AD reactor, (a) schematic of the SS-AD reactor comprising a reaction vessel and a cover; (b) schematic showing a front view of the cover apart from the reactor vessel; (c) schematic showing a top view of the reactor vessel.

The SS-AD reactor of an exemplary embodiment can be any types of air tight container. FIGS. 3A-C shows a schematic of an SS-AD reactor from an exemplary embodiment. As shown in FIG. 3A, the SS-AD reactor 25 may comprise a reaction vessel 30 and a cover 33. Supplemental effluent may enter the SS-AD reactor 25 through an effluent inlet 129 on the cover 33. Once inside reactor 25, the supplemental effluent may be added through injection pipes 42.

The reactor can be heated by all methods known in the art, for example, a water jacket and or positioning the reactor in a heated tunnel, etc. As shown in FIG. 3A, the reactor vessel 30 may be an open top (e.g., rectangular- or oval-shaped) container on wheels 38 or rollers. The wheels 38 or rollers on the reaction vessel will allow it to be easily moved into or out of a heated tunnel. The reactor vessel 30 may comprise a sealed side door (not shown) so that the digestate can be removed from the vessel when the process is complete. Once the reactor is loaded with materials, the cover can be lowered using vertical guides (not shown). The cover may comprise a self-sealing gasket design between the edges of the cover and the reaction vessel to prevent oxygen from entering and biogas from escaping. The portion of injection pipes 42 that is immersed into the materials may be perforated (dotted portion) to allow optimal distribution of the effluent into the SS-AD reactor 25. The biogas produced can vent out through a biogas outlet 132. The biogas produced from the SS-AD process can be collected and directed to the combined heat and power (CHP) unit (see FIG. 1).

For clarity, FIG. 3B shows a front view of the cover alone removed from the reactor vessel. The cover may have injection pipes 42 extending from it to deliver the effluent into the biomass during the SS-AD process. The portion of injection pipes 42a which is immersed into the materials may comprise perforations (dotted line) to allow optimal distribution of the supplemental effluent into the SS-AD reactor. When the reaction vessel is loaded with materials, the cover 33 may be lowered with vertical guides. The injection pipes 42 may penetrate into the biomass. A cover plate 49 may have a self-sealing gasket design between the edges of the cover 33 and the reaction vessel (see FIG. 3a), preventing oxygen from entering and biogas from escaping. The biogas produced may vent out through a biogas outlet 132.

FIG. 3C shows a plan view of the reactor cover plate 49 apart from the reactor cover. Cover plate 49 defines at least one opening 42a for an injection pipe. The cover plate may also have one or more aperture 132a to allow the biogas to exit through the outlet pipe.

An optional alkali pretreatment has been shown to facilitate SS-AD digestion of ligno-cellulosic biomass. If utilized, the alkali pretreatment may be conducted separately or simultaneously with the digestion process.

Figure 4:
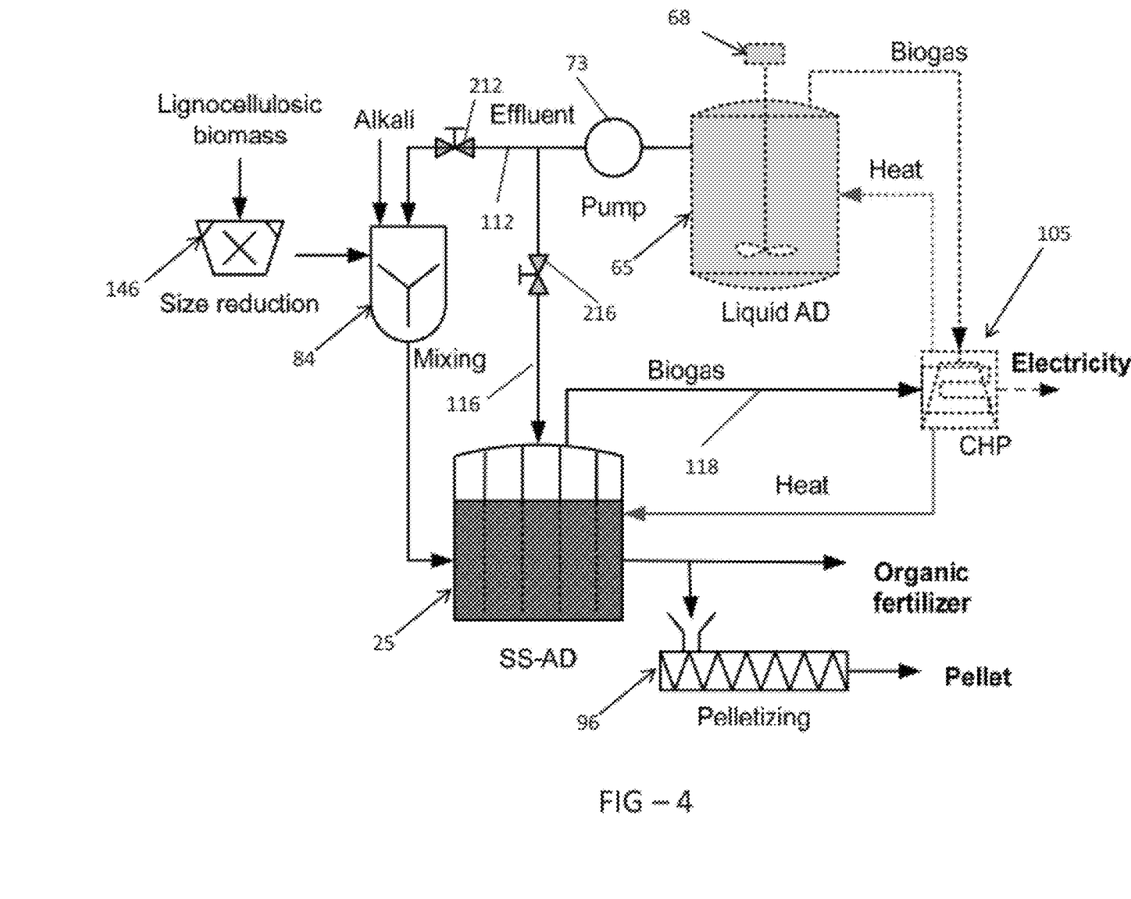
FIG. 4 is a schematic drawing of an embodiment in which pretreatment (e.g., alkali) is conducted simultaneously with the SS-AD process.

As shown in FIG. 4, for the simultaneous pretreatment and digestion process, alkali may be added while mixing the liquid AD effluent and the cellulosic biomass in mixing chamber 84. Accordingly, the cellulosic biomass, effluent, and alkali (if added) may be mixed in one step before the incubating stage. Using the configuration shown in FIG. 4, alkali (0.03-0.05 g/g of dry corn stover) was added during the mixing of corn stover and liquid AD effluent and a biogas yield of 0.35-0.40 $m^3$/kg of volatile solids (VS) was obtained at mesophilic temperature (37° C.) after 30 days of SS-AD batch operation. Repeated elements from FIG. 1 are not discussed. The embodiment is shown with the optional supplemental effluent line 116 including a supplemental effluent valve 216 to regulate the flow of supplemental effluent into the SS-AD reactor 25.

Figure 5:
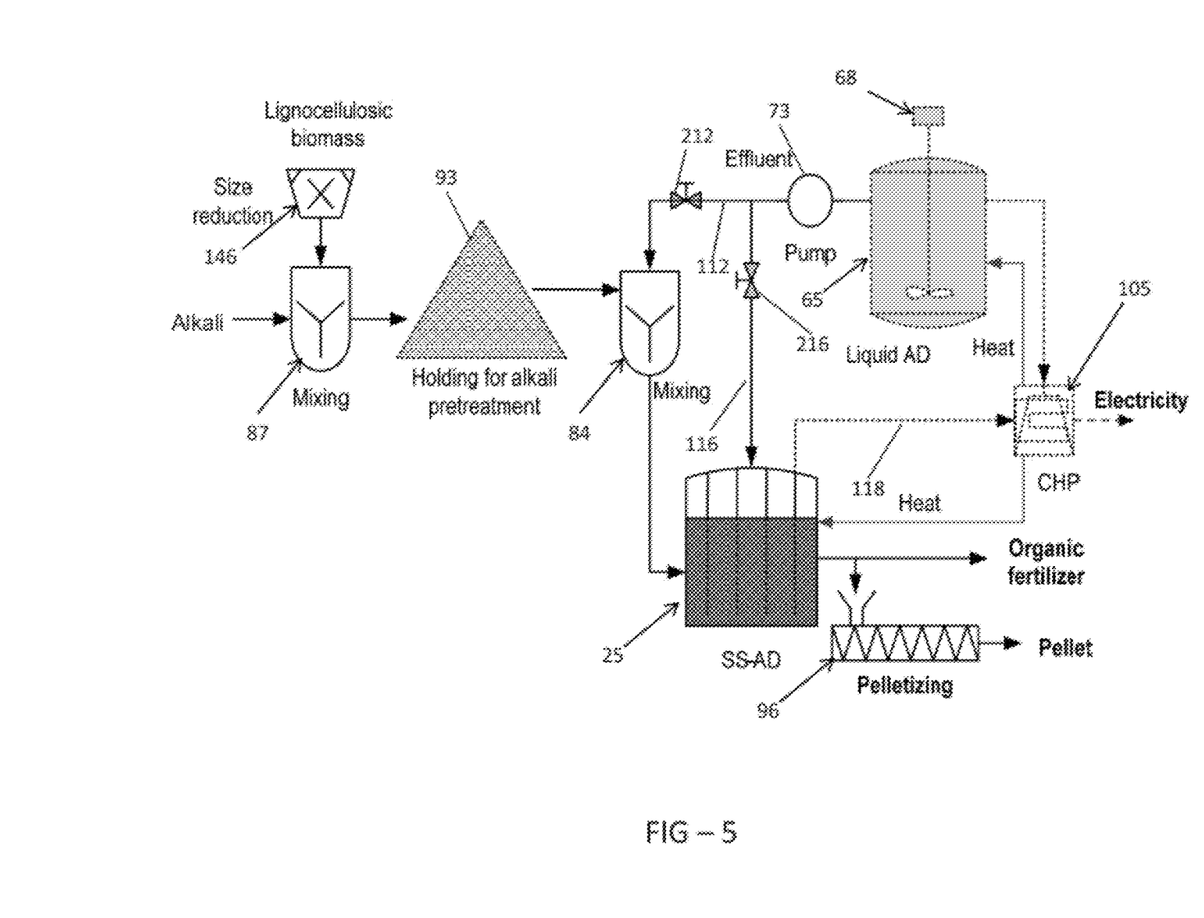
FIG. 5 is a schematic drawing of an embodiment in which pretreatment is conducted (e.g., alkali) in a separated stage.

Referring to FIG. 5, in an alternative embodiment, the cellulosic biomass may be pretreated with alkali prior to mixing with effluent. Alkali, another chemical, and or a biological agent may be added into a pretreatment mixing chamber 87. After mixing in chamber 87, the biomass may be kept in a pretreatment holding chamber 93 before entering mixing chamber 84. Repeated elements from FIG. 1 are not discussed. The embodiment is shown with the optional supplemental effluent line 116 including a supplemental effluent valve 216 to regulate the flow of supplemental effluent into the SS-AD reactor 25.

When lignocellulosic biomass is pretreated with alkali, the alkali loading rate may be 1-5% of dry matter of lignocellulosic biomass (preferable 3-5%). An optimal alkali adding ratio is important to obtain an appropriate tradeoff between biogas yield and chemical cost for different feedstock. In a preliminary test, 0.03-0.05 g NaOH/g corn stover was added. A cheaper alkali source such as $Ca(OH)_2$ may also be used effectively. Alternatively, pretreatment of lignocellulosic biomass may be conducted simultaneously with the solid state fermentation in the SS-AD reactor.

As starting material for the SS-AD, any organic solid material, including a ligno-cellulosic biomass, may be used. Appropriate feedstocks include agricultural wastes (such as corn stover, wheat straw, soybean straw, rice straw, seed hulls, sugarcane leavings, bagasse, nutshells, and manure (e.g. from cattle, poultry, and hogs)), woody materials (such as wood or bark, sawdust, timber slash, leaves, and mill scrap), municipal waste (such as waste paper and yard clippings), and energy crops (such as poplars, willows, switchgrass, alfalfa, prairie bluestem, corn, beets, and soybean). Although any lignocellulose-containing biomass can be used, disclosed embodiments are also capable of digesting non-cellulosic organic waste as well.

Disclosed processes and systems may be used for the anaerobic digestion of many other organic materials such as, for example, dairy manure. Generally dairy manure contains a significant amount of fibers. The fibers cause many problems for the liquid AD digesters. In prior systems, fibers are often washed and separated to be used for animal bedding or other applications. However, in the disclosed embodiments, the fibers may be mixed with the liquid AD digestion effluent to produce methane in the SS-AD reactor.

Figure 6:
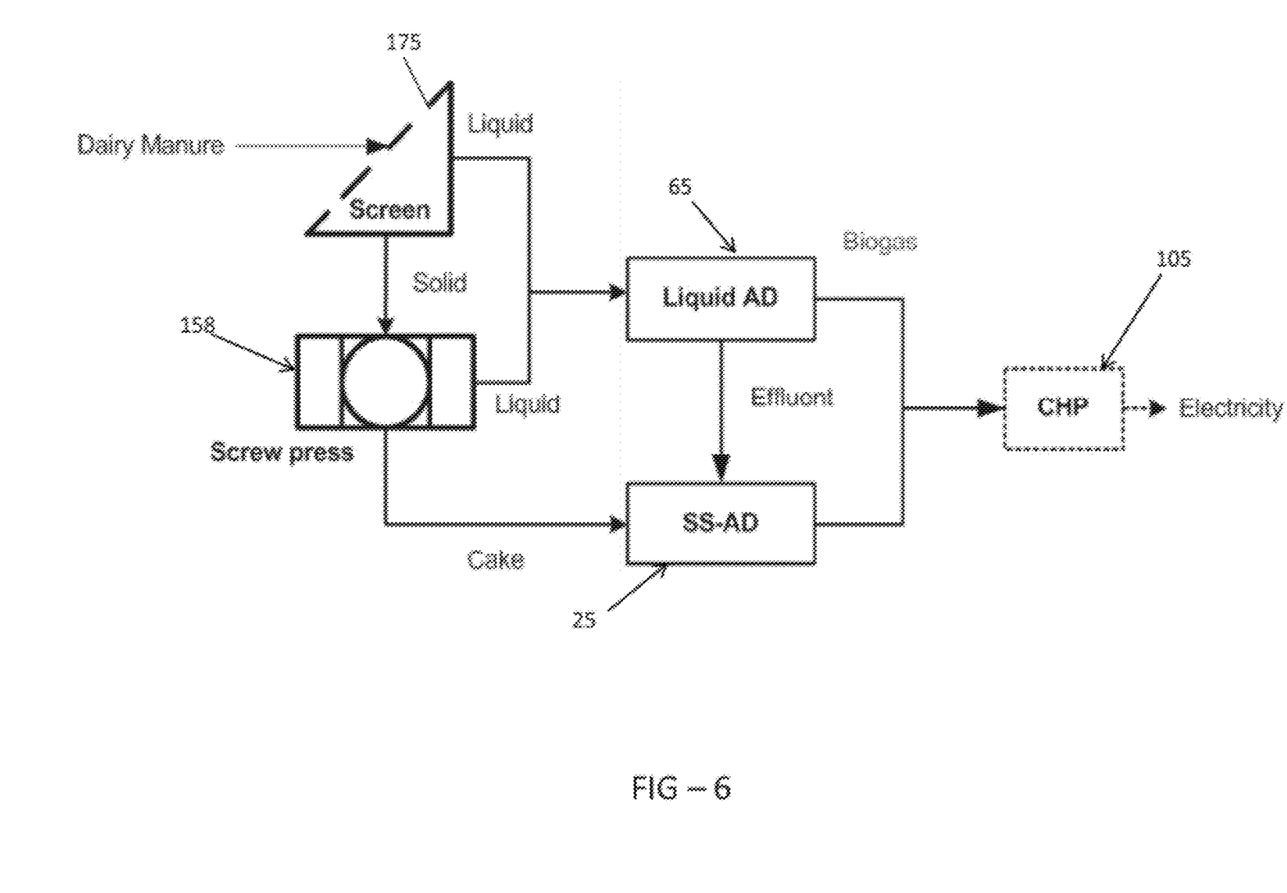
FIG. 6 is a schematic drawing of an embodiment for organic waste such as manure.

As shown in FIG. 6, dairy manure may be forced against a screen 175. The filtrate may then be directed into the liquid AD 65 to produce biogas. After screening, the fiberous solid rejected by the screen may be directed into a screw press 158 to render more digestable liquid for the liquid AD 65. The solid organic waste may then be directed to SS-AD 25. Subsequently, the cake solids resulting from the screw press 158 will be mixed with effluent of liquid AD 65 for incubation to produce biogas in the SS-AD reactor as in the embodiments using lignocellulosic biomass. A pretreatment of the fibers can also be added which can be conducted either simultaneously or separately, similar to the disclosed embodiments used to digest lignocellulosic biomass (not shown in figure).

Characterization and Utilization of SS-AD Digestate for Production of Value Added Products Effective utilization of digestate of SS-AD will provide additional revenue stream for the proposed SS-AD system. Preliminary data show that the composition of solid digestate from the disclosed embodiments contains 30-40% lignin, and 10-20% cellulose and hemicellulose which indicate that the digestate from the disclosed embodiments can be applied in the same way as compost for such uses as topsoil bedding and nursery greenhouse bulk soil. In addition, it can be pelletized for energy use.

Similar data obtained for swine manure digestate (solid fraction of liquid AD effluent) indicate that the physical properties, such as total porosity, air capacity, and water holding capacity are satisfactory for use as a plant growth medium substance.

Energy use is another proposed application for the digestate of SS-AD. Biomass pelletization is a process widely used by the renewable fuel industry to produce biomass fuels for direct combustion. The pelletization process reduces the volume of biomass in order to increase convenience and reduce cost of transportation and handling of biomass. It significantly reduces the volume of biomass, decreases the moisture content, and increases the density, as well as maintains a relatively higher heating value. Such a use will overcome three main obstacles of the biomass use in energy generation: handling, storage and transportation. The digestate from the disclosed embodiments have less moisture content compared to the solid fraction of digestate of liquid AD and the digestate of SS-AD which use leachate recycle. Implementation of the disclosed embodiments significantly reduce the energy needed for drying operation, which will make net energy balance favorable to a positive output. A typical biomass pelletizing operation consists of three major unit operations: drying, size reduction, and densification (pelletization).

Improvements in Energy Efficiency and Economics of the Biomass Energy

The embodiments of the disclosed anaerobic digestion system(s) are net energy-producing processes. In the liquid AD side of an embodiment of the system, the plant electric requirement (parasitic electric load) is about 15% of the electricity production. The higher energy requirement for the wet AD is related to the need of continuous mixing in the liquid AD reactor. The parasitic electric load of the SS-AD system is estimated to be about 10% of the energy produced by the SS-AD process when the optional CHP unit is used.

Figure 7:
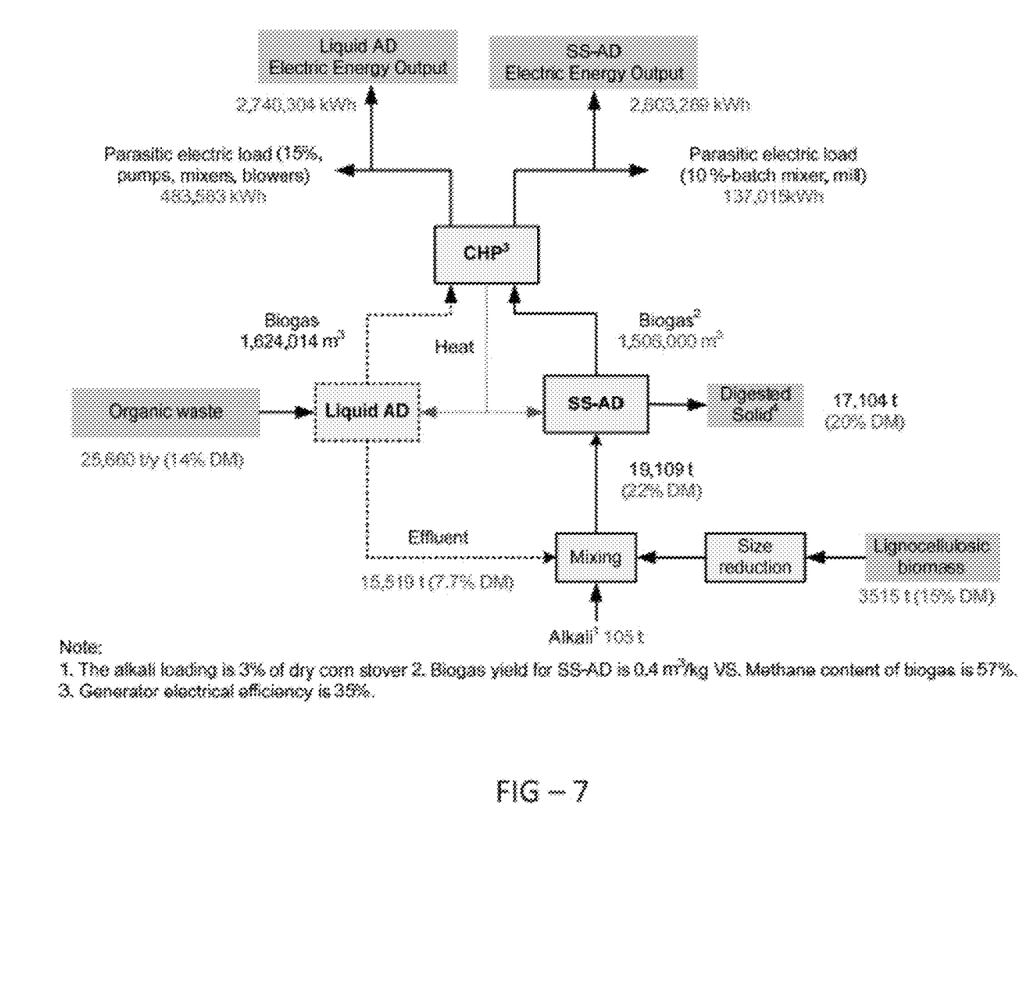
FIG. 7 is a schematic showing estimated energy and material balance for an exemplary embodiment.

As illustrated in FIG. 7, the total annual electric energy output of an embodiment of the SS-AD system is estimated to be 2,603,289 kWh. The lignocellulosic biomass feedstock needs to be collected and transported to the AD facility. The transportation of biomass needs fossil energy input in the proposed system. Based on the analysis of Sokhansanj & Fenton (2006), the energy consumption of the transportation operations are 0.77 GJ/t (0.094, 0.471, and 0.208 GJ/t for load, travel, and unload, respectively). A variable travel distance of between 10 and 60 miles was used to calculate the energy consumption for the travel operation. To deliver 3,515 tons of lignocellulosic biomass (1,715 tons of crop residues and 1,800 tons of yard waste) to the SS-AD system each year, it requires a total fossil energy input of 2,717 GJ annually. The marketable electric energy output from the SS-AD system is expected to be 9,372 GJ per year. As a result, the net energy output of an embodiment of the SS-AD system(s) is expected to be 6,655 GJ each year.

A cost analysis was also conducted based on disclosed embodiments. Labor for operation and maintenance of the system accounted about 50% of the total cost for electricity production. Feedstock is a second major cost for methane production using the proposed SS-AD system. Based on the analysis of Sokhansanj & Fenton (2006), the cost of transportation operation is $13.4/ton (load ($2.23/ton), transport ($10.11/ton), and unload ($1.06/ton), respectively. This cost was obtained based on transporting bales for a variable distance of between 10 and 60 miles (Sokhansanj & Fenton, 2006). The electricity production cost for the proposed system with a scale of 20,000 tons/year is about $0.08/kWh. This cost can be further reduced with the optimization of system design and operational parameters.

Based on a cost analysis of 9 liquid anaerobic digestion plants on dairy farms, the electricity generation cost range from $0.10 to $0.37/kWh, which is higher than the calculated production cost of $0.08 kWh of embodiments of the SS-AD system(s). Additionally, cost analysis of the liquid AD system did not add the post-AD effluent treatment cost. When sewage sludge or other food waste streams are used in the liquid AD, generally land application of the effluent is not available. High effluent handling cost makes the liquid AD system uneconomical. However, embodiments of the SS-AD system(s) use the effluent of liquid AD as inoculum and nitrogen source, which will in turn reduce the electricity production cost of the liquid AD portion of the system(s).

Embodiments of the system(s) are also more economical than regular SS-AD systems as effluent of liquid AD is used for inoculation and nitrogen sources. If effluent is not used as inoculation materials, generally there are two solutions to inoculate the raw materials. One solution is to recycle the digestate with volume 5-6 times of raw feedstock, however, this requires an increase the total reactor size by 5-6 times. To obtain the same amount of electricity output, the electricity production cost will increase about $0.25 per kWh due to the increase of reactor size and related increase in maintenance and operational cost.

For systems not using digestate recycle, leachate recycle is generally used to inoculate the raw materials. To obtain the leachate, water needs to be added, which will reduce the solid content of the digestate. Treatment of digestate is required before it can be transported, which also substantially increases the system cost of conventional systems. Also 4% of $NH_4Cl$ needs to be added as nitrogen source when lignocellulosic biomass is converted in the traditional SS-AD system. When effluent of liquid AD is used as nitrogen source in the disclosed embodiments of the SS-AD system(s), it saves $0.04-$0.05 for one kWh electric energy produced. Additional savings is realized in the disclosed embodiments due to reduced capital and operational cost, as the pretreatment of lignocellulosic biomass may be conducted simultaneously in the SS-AD process.

Environmental Benefits of Various Embodiments

Using the liquid AD effluent in the SS-AD system(s) has a significant benefit over sending it to composting as it helps in odor control and reducing the discharge of wastewater. Compared to composting, volatile organic carbons (VOCs) are broken down in the anaerobic digester and combusted in a controlled environment. As there is no waste liquid stream generated from the disclosed embodiments, it reduces the water pollution caused by liquid effluent in the liquid AD system or leachate in the composting system.

The disclosed embodiments also have the potential to improve public health generally. Organic wastes, mainly animal waste and municipal sludge, are often the source of pathogens which can contaminate the food and or water sources. Digesting the waste stream anaerobically minimizes the pathogen populations and reduces the possibility of contamination. If liquid AD effluent is used in the disclosed embodiments, it will also remove the hazard of flocculants added during treatment of liquid AD effluent.

Oil and Fossil Fuel Displacement of Various Embodiments

An energy analysis of a 2,000 ton/year SS-AD system indicated that the net energy output of the system is expected to be 6,655 GJ per year, which is equivalent to 45,420 gallons of diesel oil. In addition, this system uses effluent of liquid AD as nitrogen source. It saves 120 tons of $NH_4Cl$/yr for the 2,000 tons/year system, which will reduce the import of fossil fuel and energy for the production of $NH_4Cl$.

Rural Economic Development

The proposed SS-AD system is a distributed farm scale system which can be installed on farm to handle the effluent of a liquid AD system. This proposed SS-AD system uses effluent of liquid AD as inoculum and nitrogen source, which will reduce the overuse of AD effluent on the farm land. As a result, the land sustainability will be increased. Compared to the SS-AD system which can only use corn silage as feedstock, this system uses crop residues and yard waste to produce methane, which will also increase the land sustainability and reduce the burden on land for food and energy production.

What is claimed is:

1. A method of controlling the production of biogas from both solid and liquid organic biomass, comprising the steps of:
    generating an effluent from the liquid organic biomass in a first vessel, operating as a liquid anaerobic digester;
    combining the effluent with the solid organic biomass, producing an effluent-biomass mixture;
    incubating, in a second vessel, operating as a solid waste digestion reactor, the effluent-biomass mixture to produce a biogas and a digestate; and
    controlling, by use of the effluent, the incubating step in the second vessel
    wherein the first and second vessels are in fluid communication or in series communication with each other by a conduit that connects an outlet of the first vessel to an inlet of the second vessel, the conduit also having an inlet along the conduit to admit the solid organic biomass for the combining step and to deliver the effluent-biomass mixture to the second vessel.

2. The method of claim 1, wherein:
    the combining step is performed external to the solid waste digestion reactor vessel.

3. The method of claim 2, further comprising the step of:
    treating the solid organic biomass with alkali prior to the combining step.

4. The method of claim 2, wherein:
    the combining step is performed in a mixing chamber, located along the conduit that connects the outlet of the first vessel to an inlet of the second vessel, comprising means for mixing the solid organic biomass with the effluent.

5. The method of claim 2, further comprising the step of:
    cutting or grinding the solid organic biomass prior to the combining step.

6. The method of claim 5, wherein:
    the cutting or grinding step provides a particulate material having an average size in the range of from about 2 millimeters to about 50 millimeters.

7. The method of claim 1, wherein:
the solid organic biomass comprises a lignocellulosic material.

8. The method of claim 1, further comprising the step of:
treating the solid organic biomass with alkali prior to the combining step.

9. The method of claim 1, further comprising the step of:
dewatering the liquid anaerobic digester effluent prior to the combining step.

10. The method of claim 1, wherein:
the incubating step further comprises the substep of:
adding a supplemental portion of the liquid anaerobic digester effluent to the effluent-biomass mixture during the incubating step.

11. The method of claim 10, wherein:
the adding substep is performed intermittently during the incubating step.

12. The method of claim 1, further comprising the step of:
cutting or grinding the solid organic biomass prior to the combining step.

13. The method of claim 12, wherein:
the cutting or grinding step provides a particulate material having an average size in the range of from about 2 millimeters to about 50 millimeters.

14. The method of claim 1, wherein:
the controlling of the incubating step is achieved by at least one of:
adjusting the ratio of the solid organic biomass to the effluent in the combining step;
adjusting a solids content of the effluent by dewatering; and
adding the effluent directly to the solid waste digestion reactor vessel during the incubating step.

15. The method of claim 1, further comprising the step of:
removing the biogas and digestate from the second vessel.

16. The method of claim 15, further comprising the step of:
directing the produced biogas to a combined heat and power unit.

17. The method of claim 15, wherein:
none of the digestate is recycled into the effluent-biomass mixture in the second vessel.

* * * * *